(12) United States Patent
Sugiyama et al.

(10) Patent No.: US 9,693,726 B2
(45) Date of Patent: Jul. 4, 2017

(54) ALERTNESS DEVICE, SEAT, AND METHOD FOR DETERMINING ALERTNESS

(71) Applicants: TS TECH CO., LTD., Asaka-shi, Saitama (JP); PUBLIC UNIVERSITY CORPORATION NAGOYA CITY UNIVERSITY, Nagoya-shi, Aichi (JP)

(72) Inventors: Shinji Sugiyama, Tochigi (JP); Takayoshi Ito, Tochigi (JP); Kiyoko Yokoyama, Aichi (JP); Issey Takahashi, Aichi (JP)

(73) Assignees: TS Tech Co., Ltd., Saitama (JP); Public University Corporation Nagoya City University, Aichi (JP)

( * ) Notice: Subject to any disclaimer, the term of this patent is extended or adjusted under 35 U.S.C. 154(b) by 0 days.

(21) Appl. No.: 15/030,734

(22) PCT Filed: Oct. 20, 2014

(86) PCT No.: PCT/JP2014/077871
§ 371 (c)(1),
(2) Date: Apr. 20, 2016

(87) PCT Pub. No.: WO2015/060267
PCT Pub. Date: Apr. 30, 2015

(65) Prior Publication Data
US 2016/0249843 A1    Sep. 1, 2016

(30) Foreign Application Priority Data
Oct. 21, 2013    (JP) ................................. 2013-218702

(51) Int. Cl.
*A61B 5/04* (2006.01)
*A61B 5/18* (2006.01)
(Continued)

(52) U.S. Cl.
CPC .............. *A61B 5/18* (2013.01); *A61B 5/0245* (2013.01); *A61B 5/02405* (2013.01);
(Continued)

(58) Field of Classification Search
CPC .. B60K 28/06; B60W 2040/0827; A61B 5/18; A61B 5/02405; A61B 5/02455; A61B 5/0456; A61B 5/6893; A61B 5/4809
See application file for complete search history.

(56) References Cited

U.S. PATENT DOCUMENTS

| 7,512,439 | B1 | 3/2009 | Farazi |
| 2009/0209829 | A1 | 8/2009 | Yanagidaira et al. |

(Continued)

FOREIGN PATENT DOCUMENTS

| EP | 2 092 889 A1 | 8/2009 |
| EP | 2 441 387 A1 | 4/2012 |

(Continued)

OTHER PUBLICATIONS

Extended European Search Report issued in related application EP 14855514.7, Oct. 7, 2016, 10 pages.

(Continued)

*Primary Examiner* — Robert N Wieland
(74) *Attorney, Agent, or Firm* — Drinker Biddle & Reath LLP

(57) ABSTRACT

An alertness device includes a heart rate sensor configured to obtain an electrocardiographic signal of a person, a calculation unit configured to calculate the electrocardiographic signal obtained from the heart rate sensor, a waveform generation unit configured to generate an RRI waveform from an electrocardiographic waveform of the electrocardiographic signal, and a determination unit configured to determine the alertness of the person based on the electrocardiographic signal. The calculation unit replicates a same number of RRI waveforms as that of anchors, each anchor being a point where a certain RRI is shorter than an
(Continued)

adjacent preceding RRI, moves the time axes of the replicated RRI waveforms such that the anchors of the replicated RRI waveforms are in phase with each other, and calculates a PRSA signal defined as an RRI average for each time axis. The determination unit determines the alertness based on the RRIs and the PRSA signals.

10 Claims, 8 Drawing Sheets

(51) Int. Cl.
    *A61B 5/0245*     (2006.01)
    *A61B 5/00*     (2006.01)
    *A61B 5/024*     (2006.01)
    *A61B 5/0456*     (2006.01)
    *A61B 5/16*     (2006.01)

(52) U.S. Cl.
    CPC ........ *A61B 5/02455* (2013.01); *A61B 5/0456* (2013.01); *A61B 5/6893* (2013.01); *A61B 5/7264* (2013.01); *A61B 5/168* (2013.01); *A61B 2503/22* (2013.01)

(56) References Cited

U.S. PATENT DOCUMENTS

| | | |
|---|---|---|
| 2010/0049066 A1 | 2/2010 | Hatakeyama |
| 2012/0078122 A1* | 3/2012 | Yokoyama ........... A61B 5/0245 600/484 |
| 2013/0253841 A1 | 9/2013 | Matsunaga et al. |
| 2014/0371603 A1 | 12/2014 | Fujita et al. |

FOREIGN PATENT DOCUMENTS

| | | |
|---|---|---|
| JP | 11-314534 A | 11/1999 |
| JP | 3271448 B2 | 4/2002 |
| JP | 4697185 B2 | 6/2011 |
| JP | 2013-192759 A | 9/2013 |
| WO | 00/44580 A | 8/2000 |
| WO | 2007/091199 A2 | 8/2007 |
| WO | 2013/077253 A1 | 5/2013 |

OTHER PUBLICATIONS

Bauer et al., "Deceleration capacity of heart rate as a predictor of mortality after myocardial infarction: cohort study," The Lancet, The Lancet Publishing Corp., GB, May 20, 2006, vol. 367(9523), pp. 1674-1681.

Bauer et al., "Phase-rectified signal averaging detects quasi-periodicities in non-stationary data," Physica A, North-Holland, Amsterdam, NL, May 15, 2006, vol. 364, pp. 423-434.

Takahashi et al., "Development of a Feedback Stimulation for Drowsy Driver Using Heartbeat Rhythms," 33rd Annual International Conference of the IEEE Engineering in Medicine and Biology Society, IEEE, Aug. 30, 2011, pp. 4153-4158.

\* cited by examiner

RRIm(t) > RRIm(t+1)

$\alpha * ACm(t) > ACm(t+1)$

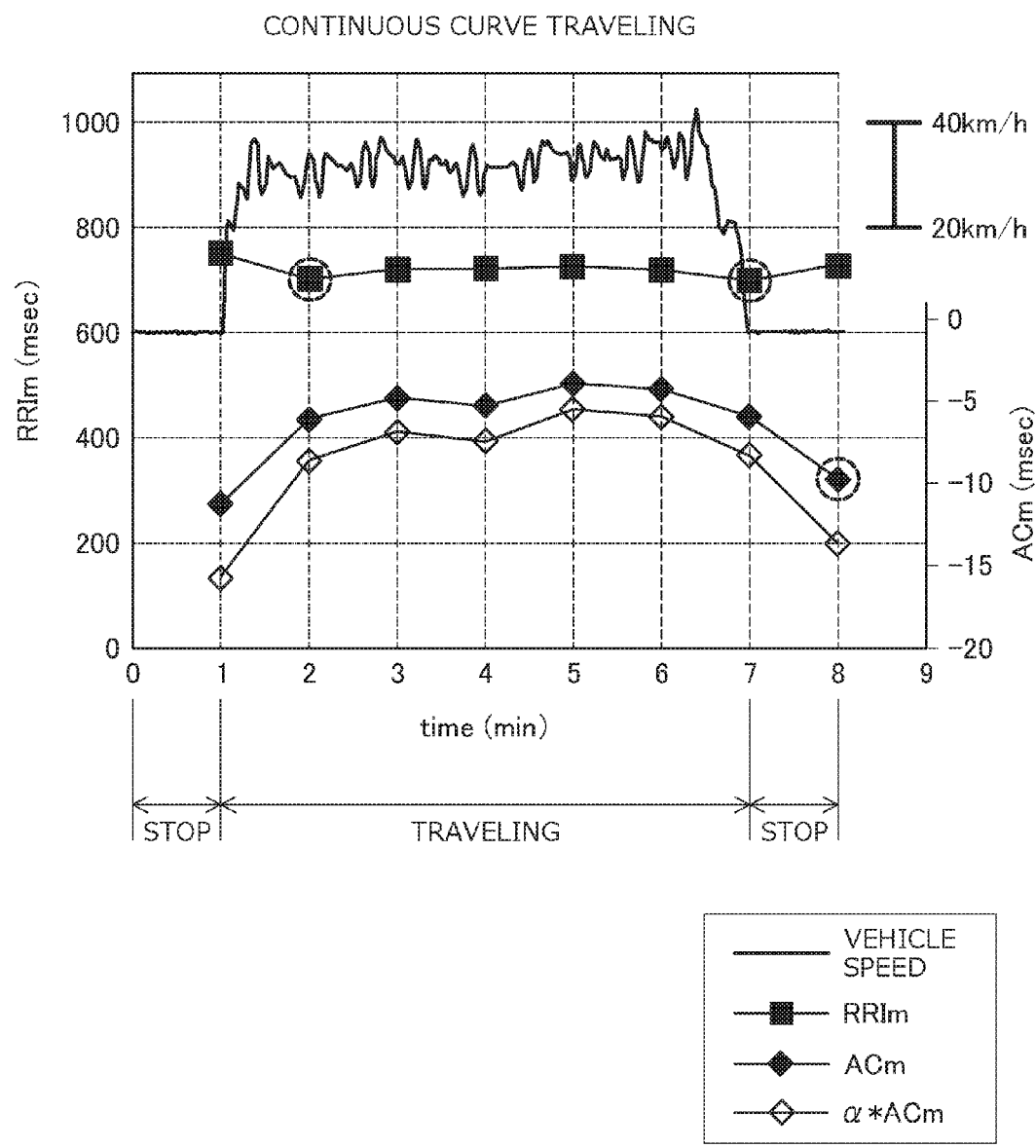

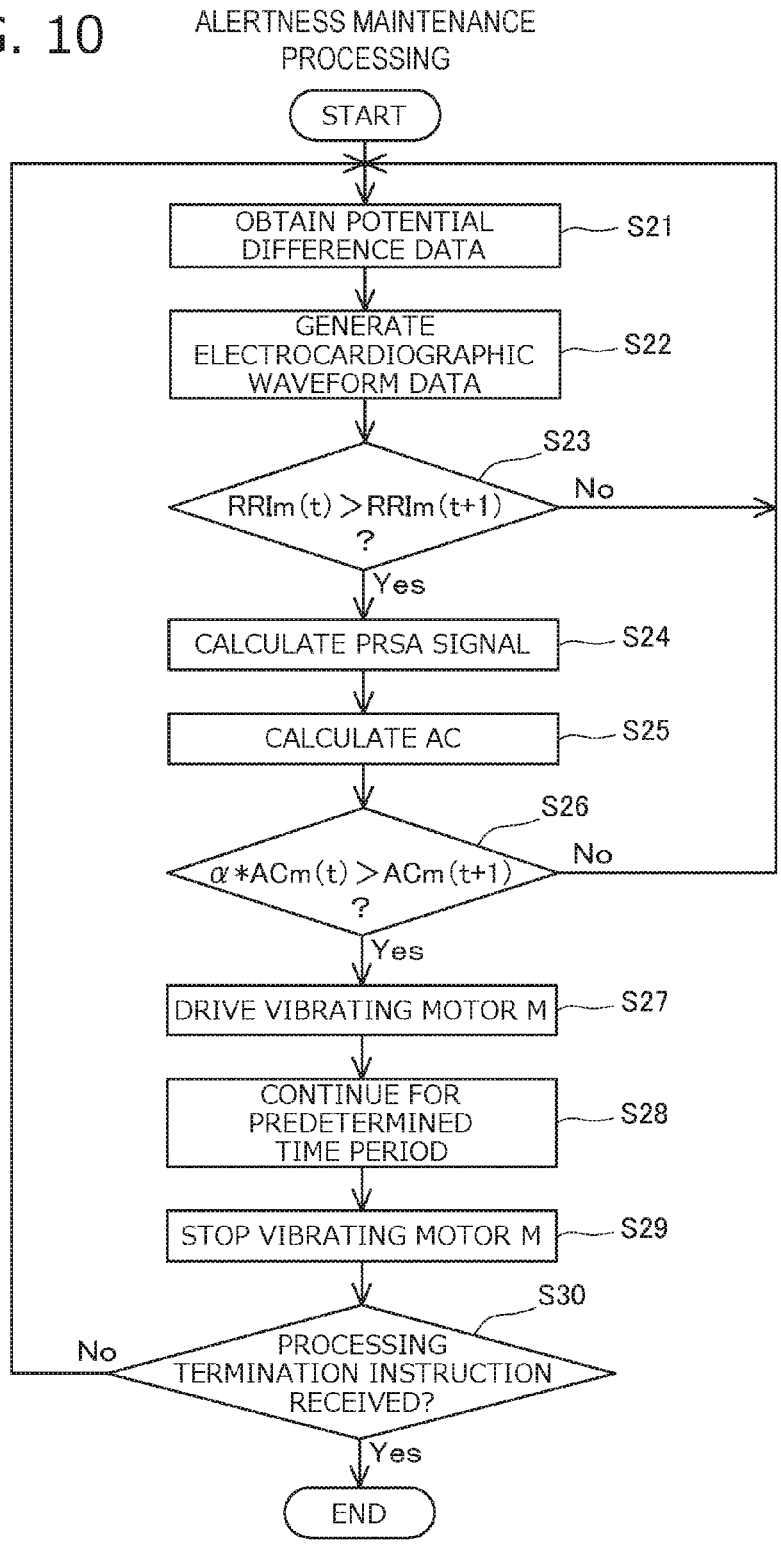

ALERTNESS DEVICE, SEAT, AND METHOD FOR DETERMINING ALERTNESS

CROSS-REFERENCE TO RELATED APPLICATIONS

This application is a National Stage Entry application of PCT Application No. PCT/JP2014/077871, filed Oct. 20, 2014, which claims the priority benefit of Japanese Patent Application No. 2013-218702, filed on Oct. 21, 2013, the contents being incorporated herein by reference.

BACKGROUND

Various embodiments of the present disclosure relate to an alertness device, a seat including the alertness device, and an alertness determination method. In particular, the present disclosure relates to an alertness device having the function of determining alertness, and a seat including the alertness device, and an alertness determination method.

In recent years, a change in a driver's physical condition needs to be detected for stable vehicle operation. Various techniques of detecting and calculating various parameters indicating a driver's state to determine the change in the physical condition, particularly alertness, have been proposed.

For example, Japanese Patent No. 4697185 discloses the following technique. A cardiac cycle sequence is obtained from a heart rate signal, and fast Fourier transformation is performed for the cardiac cycle sequence. The resultant power spectrum is repeatedly integrated to obtain a heart-rate fluctuation low-frequency component power. Driver's alertness is determined based on the heart-rate fluctuation low-frequency component power.

Moreover, Japanese Patent No. 3271448 discloses the following technique. A threshold is first calculated in such a manner that in an awake period, an average of R-R intervals (RRIs) for a predetermined heart rate or a predetermined period of time is obtained, and then a value of integral of an RRI exceeding the average is multiplied by a predetermined factor. Of the RRIs obtained as described above, the RRI(s) exceeding the average is integrated. When such an integrated value exceeds the threshold, it is determined that alertness is lowered.

According to the technique of Japanese Patent No. 4697185, fast Fourier transformation and integration of the power spectrum need to be repeated to calculate the heart-rate fluctuation low-frequency component power as the indicator for determining the presence/absence of drowsiness. Such analysis processing requires time. For this reason, alertness determination is delayed, leading to a delay in notification to a seated passenger. With lack of data continuity, an accurate result cannot be obtained. This leads to a lower robustness such as inexecutable detection due to a missing value and noise contamination and rapid lowering of an accuracy.

According to the technique of Japanese Patent No. 3271448, only the value of integral of the RRI is used as the indicator for determining the alertness. Such alertness determination depends on an RRI within an integral range. For this reason, a detection accuracy is low. In some cases, the sympathetic nerve is instantaneously activated against drowsiness when the drowsiness is initially caused, for example. In this case, the RRI value might be instantaneously lowered in association with activation of the sympathetic nerve. According to the technique of Japanese Patent No. 3271448 using, as a criteria for determination, the value obtained by integration of such an instantaneously-lowered RRI, it is difficult to accurately determine the alertness. For this reason, an alertness device configured such that a load is low in the processing for alertness determination and that the accuracy in alertness determination is high, a seat including the alertness device, and an alertness determination method have been demanded.

SUMMARY

The present disclosure has been made in view of the above-described problem, and some embodiments are intended to provide an alertness device configured such that a load is low in the processing for alertness determination and that the accuracy in alertness determination is high, a seat including the alertness device, and an alertness determination method. Further, some embodiments of the present disclosure are also intended to favorably maintain person's alertness based on accurate alertness determination.

The above-described problem is solved by an alertness device of a first embodiment of the present disclosure. The alertness device of the first embodiment of the present disclosure includes a heart rate sensor configured to obtain an electrocardiographic signal of a person, a calculation unit configured to calculate the electrocardiographic signal obtained from the heart rate sensor, a waveform generation unit configured to generate, from an electrocardiographic waveform of the electrocardiographic signal, an RRI waveform showing transition for a predetermined time period with RRIs, each RRI being an R-R interval between R-waves, and a determination unit configured to determine the alertness of the person based on the electrocardiographic signal. The calculation unit replicates the same number of RRI waveforms as that of anchors, each anchor being a point where a certain RRI is shorter than the adjacent preceding RRI in the RRI waveform generated by the waveform generation unit, moves the time axes of the replicated RRI waveforms such that the anchors of the replicated RRI waveforms are in phase with each other, and calculates a phase-rectified signal averaging signal, which is a PRSA signal, defined as an RRI average for each time axis. The determination unit determines, based on the RRIs and the PRSA signals, whether the person is in an alert state or an unalert state.

As described above, the determination unit determines the alert state or the unalert state of the person based on the RRIs and the PRSA signals. Thus, a processing load can be more reduced as compared to the case of determining alertness by analysis of a heart rate frequency, and the person's alertness can be more accurately determined as compared to the case of determining alertness based only on RRIs.

The waveform generation unit preferably generates a PRSA signal waveform based on the PRSA signals. When an acceleration capacity (AC) ACn is defined by the following formula 1:

$$ACn = X(0) + X(1) - X(-1) - X(-2) \qquad \text{[Formula 1]}$$

where in the generated PRSA signal waveform, a PRSA signal at a certain anchor is defined by $X(0)$, a PRSA signal for a heart rate at the adjacent succeeding anchor of the certain anchor is defined by $X(1)$, a PRSA signal for the heart rate at the adjacent preceding anchor of the certain anchor is defined by $X(-1)$, and a PRSA signal for the heart rate at the adjacent preceding anchor of the anchor at which the $X(-1)$ is obtained is defined by $X(-2)$, the calculation unit preferably calculates, for a predetermined time period, the RRI average and an ACn average, and the determination unit preferably determines, based on the values calculated by the calculation unit, that the person is in the unalert state when a certain RRI average is less than the adjacent preceding RRI average and when a certain ACn average is less than the α-fold of the adjacent preceding ACn average. As described above, the calculation unit calculates the RRI average and the ACn average for the predetermined time period, and based on the values calculated by the calculation unit, the determination unit determines that the person is in the unalert state when a certain RRI average is less than the adjacent preceding RRI average and when a certain ACn average is less than the α-fold of the adjacent preceding ACn average. Thus, the person's alertness can be more accurately determined as compared to the case of determining person's alertness based only on RRIs.

An α is preferably 1.0 to 2.0. Since the α is 1.0 to 2.0 as described above, the person's alertness can be more accurately determined.

The calculation unit may calculate the RRI average and the ACn average for every 20- to 300-second interval, and the determination unit may determine the alertness of the person based on the RRI average and the ACn average calculated by the calculation unit. As described above, the calculation unit calculates the RRI average and the ACn average for every 20- to 300-second interval, and the determination unit determines the alertness of the person based on the RRI average and the ACn average. Thus, the person's alertness can be more accurately determined.

The α is preferably 1.4. Since the α is 1.4 as described above, the person's alertness can be more accurately determined.

The calculation unit may calculate the RRI average and the ACn average for every 60-second interval. Since the calculation unit calculates, as described above, the RRI average and the ACn average for every 60-second interval, the person's alertness can be more accurately determined.

The alertness device of the first embodiment of the present disclosure preferably further includes a notification device configured for notification to the person or one or more persons therearound, and a driver configured to drive the notification device to notify the person or the one or more persons therearound of the determination unit having determined that the person is in the unalert state. When the determination unit determines that the person is in the unalert state, the driver drives the notification device to notify the person or the one or more persons therearound of the determination result. This brings the person to the alert state, or allows the person or the one or more persons therearound to take action to maintain the person's alertness.

The above-described problem is solved by a seat of a second embodiment of the present disclosure. The seat of the second embodiment of the present disclosure includes a seat cushion on which a passenger is seated, a seat back as a back rest of the seated passenger, and the above-described alertness device. The heart rate sensor is disposed in the seat back. Since the seat includes the alertness device as described above, the alertness of the seated passenger can be more accurately determined as compared to the case of determining the alertness of a seated passenger based only on RRIs.

The above-described problem is solved by the method for determining alertness according to a third embodiment of the present disclosure. The method of the third embodiment of the present disclosure includes obtaining an electrocardiographic signal, generating, from an electrocardiographic waveform of the electrocardiographic signal, an RRI waveform showing transition for a predetermined time period with RRIs, each RRI being an R-R interval between R-waves, replicating the same number of RRI waveforms as that of anchors, each anchor being a point where a certain RRI is shorter than the adjacent preceding RRI in the generated RRI waveform, moving the time axes of the replicated RRI waveforms such that the anchors of the replicated RRI waveforms are in phase with each other, calculating a PRSA signal defined as an RRI average for each time axis, and determining, based on the RRIs and the PRSA signals, whether a person is in an alert state or an unalert state.

As described above, it is determined, based on the RRIs and the PRSA signals, whether the person is in the alert state or the unalert state. Thus, a processing load can be more reduced as compared to the case of determining alertness by analysis of a heart rate frequency, and the person's alertness can be more accurately determined as compared to the case of determining alertness based only on RRIs.

A PRSA signal waveform may be generated based on the PRSA signals. When an ACn is defined by the following formula 1:

$$ACn = X(0) + X(1) - X(-1) - X(-2) \qquad \text{[Formula 1]}$$

where in the generated PRSA signal waveform, a PRSA signal at a certain anchor is defined by $X(0)$, a PRSA signal at the adjacent succeeding anchor of the certain anchor is defined by $X(1)$, a PRSA signal at the adjacent preceding anchor of the certain anchor is defined by $X(-1)$, and a PRSA signal at the adjacent preceding anchor of the anchor at which the $X(-1)$ is obtained is defined by $X(-2)$, the RRI average and an ACn average may be calculated for a predetermined time period, and based on the calculated values, the person may be determined as being in the unalert state when a certain RRI average is less than the adjacent preceding RRI average and when a certain ACn average is less than the α-fold of the adjacent preceding ACn average. As described above, the RRI average and the ACn average for the predetermined time period are calculated, and based on the calculated values, the person is determined as being in the unalert state when a certain RRI average is less than the adjacent preceding RRI average and when a certain ACn average is less than the α-fold of the adjacent preceding ACn average. Thus, the person's alertness can be more accurately determined as compared to the case of determining person's alertness based only on RRIs.

According to various embodiments of the present disclosure, an alertness device configured so that a processing load can be more reduced as compared to the case of determining alertness by analysis of a heart rate frequency and that person's alertness can be accurately determined, a seat including the alertness device, and an alertness determination method can be provided. Moreover, according to various embodiments of the present disclosure, the person's alertness can be favorably maintained.

BRIEF DESCRIPTION OF DRAWINGS

FIG. 8 is a graph of an example change in subject's RRIm and ACm in continuous curve traveling, according to an embodiment.

FIG. 10 is a flow chart of an example of alertness maintenance processing, according to an embodiment.

DETAILED DESCRIPTION

An alertness device, a seat including the alertness device, and an alertness determination method according to various embodiments of the present disclosure are described below with reference to attached drawings.

Figure 1:
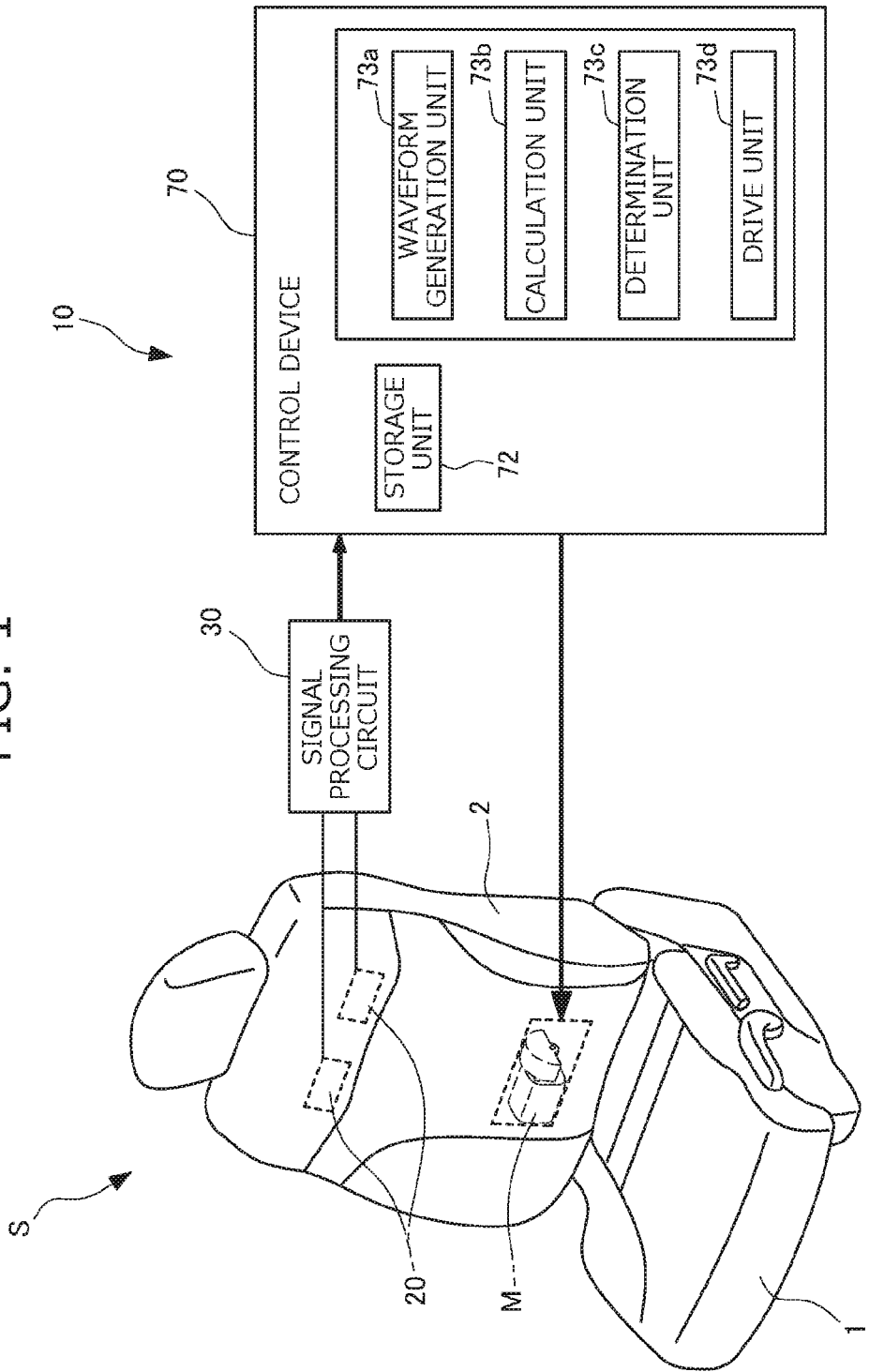
FIG. 1 is a schematic view of an entire configuration of an alertness device of an embodiment of the present disclosure, according to an embodiment.

First, an alertness device 10 of the present embodiment is described with reference to FIG. 1. FIG. 1 is a schematic view of an overall configuration of the alertness device 10 of an embodiment of the present disclosure. The alertness device 10 of the present embodiment is configured to determine the alertness of a seated passenger based on a potential difference signal for a heart rate. As illustrated in FIG. 1, the alertness device 10 of the present embodiment mainly includes a vehicle seat S having, in a seat back 2, two sheet-shaped heart rate sensors 20 and a vibration motor M, and a control device 70 connected to the heart rate sensors 20 via a signal processing circuit 30 to control the vibration motor M.

The vehicle seat S includes a seat cushion 1 on which the passenger is seated, and the seat back 2 serving as a back rest of the seated passenger. In the vehicle seat S, the heart rate sensors 20 and the vibration motor M are provided close to a seated passenger side in the seat back 2.

Each heart rate sensor 20 is a capacitive sensor, and is capacitively-coupled to the seated passenger to detect the body potential of the seated passenger. Each heart rate sensor 20 is formed of a conductive metal conductor, conductive fibers, or a conductive fabric tape.

The signal processing circuit 30 is connected to the heart rate sensors 20 and the control device 70. The signal processing circuit 30 has the function of amplifying the body potential detected by the heart rate sensors 20, outputting a potential difference signal, removing noise of the potential difference signal other than an electrocardiographic frequency, and converting the potential difference signal into a digital signal.

The control device 70 includes a storage unit 72 including a not-shown RAM, a waveform generation unit 73a functioning by execution of a program stored in the not-shown ROM by a not-shown CPU and configured to generate voltage waveform data, a calculation unit 73b configured to perform data calculation for alertness determination, a determination unit 73c configured to determine alertness, and a driver (drive unit) 73d configured to drive the vibration motor M.

The storage unit 72 is configured to temporarily store parameters contained in a signal under arithmetic control and input and output signals and to store the potential difference signal converted into the digital signal and other signals in the present embodiment. The waveform generation unit 73a is configured to generate the voltage waveform data from the potential difference signal obtained from the heart rate sensors 20. The calculation unit 73b is configured to perform later-described calculation based on the voltage waveform data generated by the waveform generation unit 73a. The determination unit 73c is configured to use, as an indicator, the data calculated by the calculation unit 73b to determine the alertness. The driver 73d is configured to drive the vibration motor M according to the determination of the seated passenger's alertness being lowered to provide vibratory stimulation to the seated passenger.

Alertness Determination Processing

Figure 2:
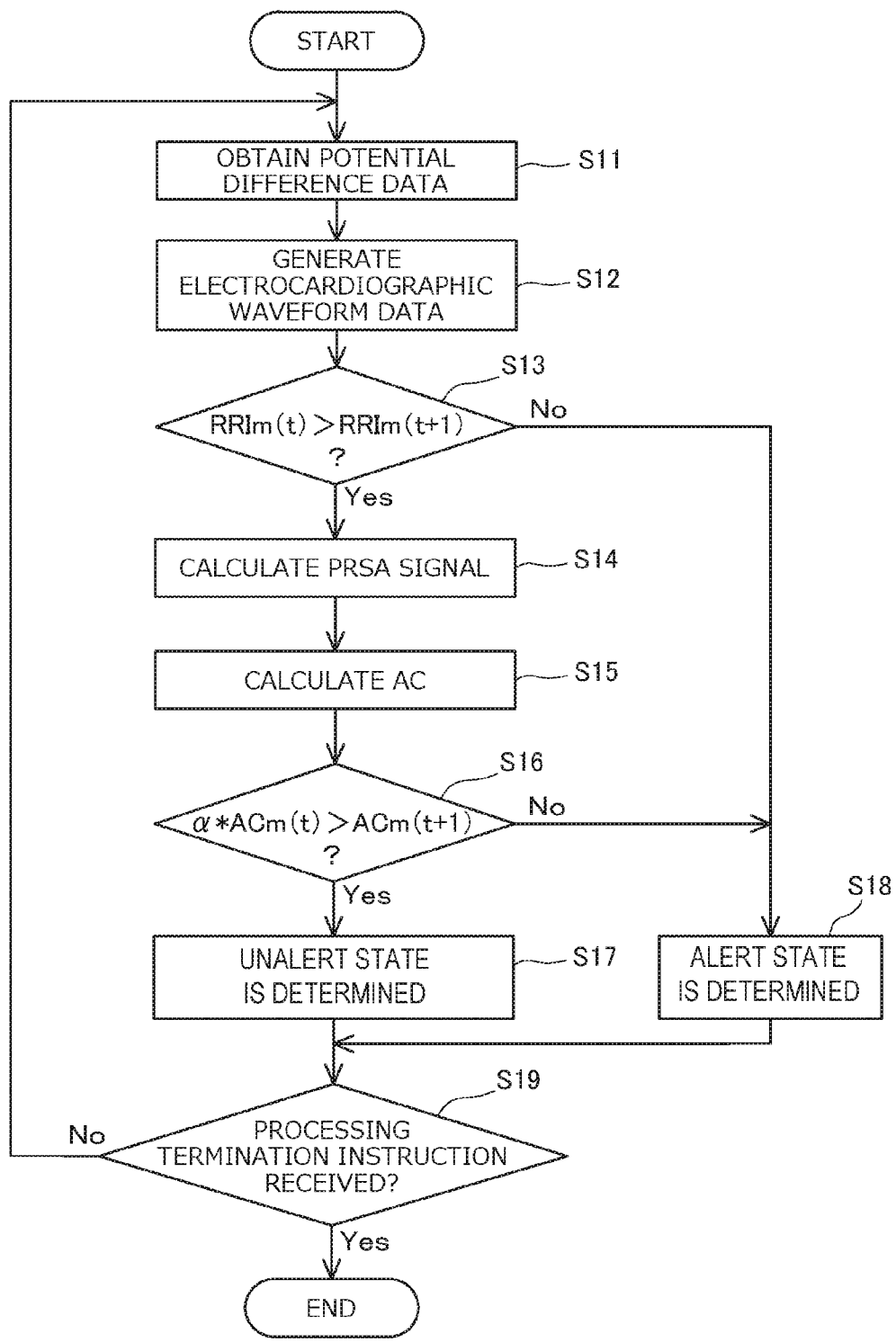
FIG. 2 is a flow chart of an example method of alertness determination processing, according to an embodiment.
Figure 3:
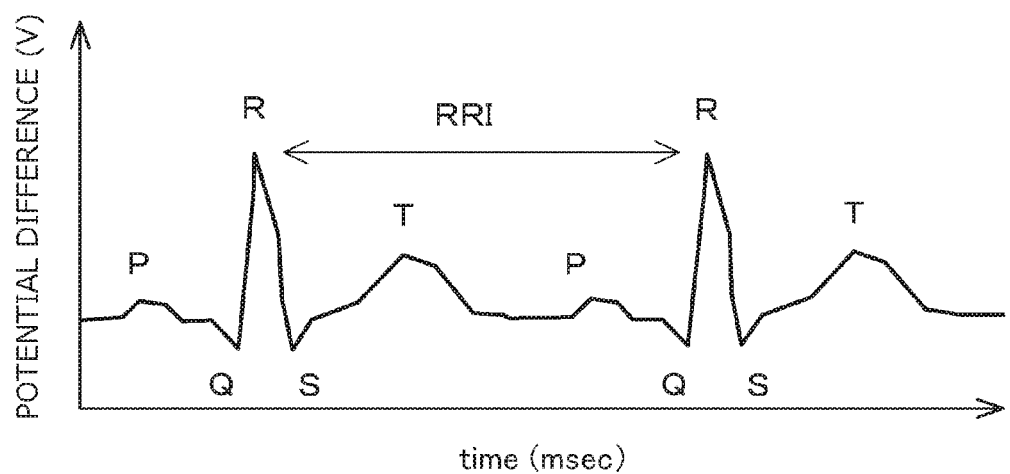
FIG. 3 is a graph of an example pattern of an electrocardiographic waveform, according to an embodiment.
Figure 4:
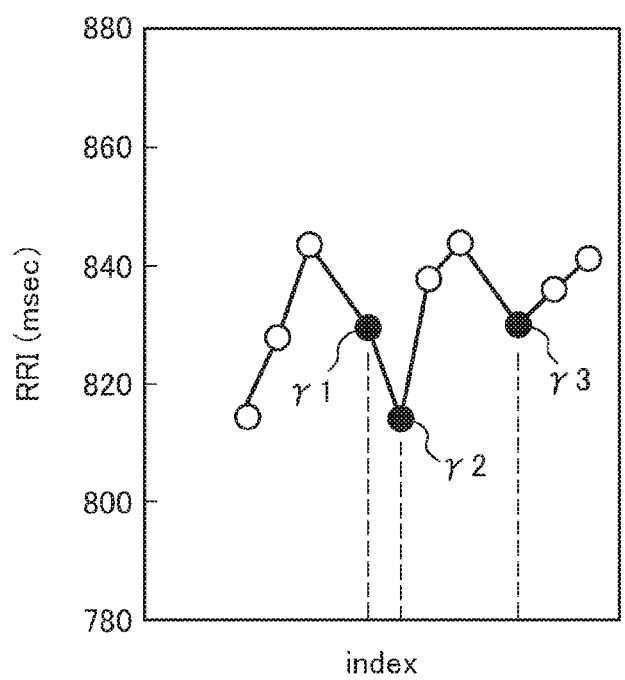
FIG. 4 is a graph of an example chronological change in an RRI, and shows, as an anchor, each point where in comparison between RRIs at adjacent time points, a latter one of the RRIs is shorter than a former one of the RRIs, according to an embodiment.
Figure 5:
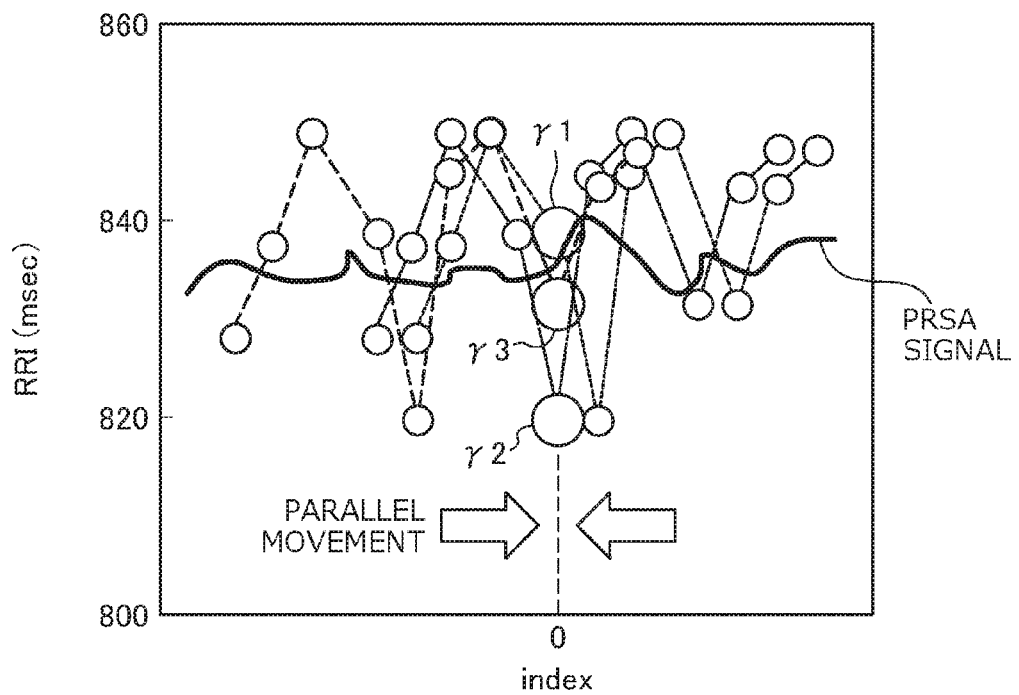
FIG. 5 is a graph in which the same number of waveforms as that of the anchors of FIG. 4 are replicated, and the time axes at the anchor points of the replicated waveforms are aligned to each other, according to an embodiment.
Figure 6:
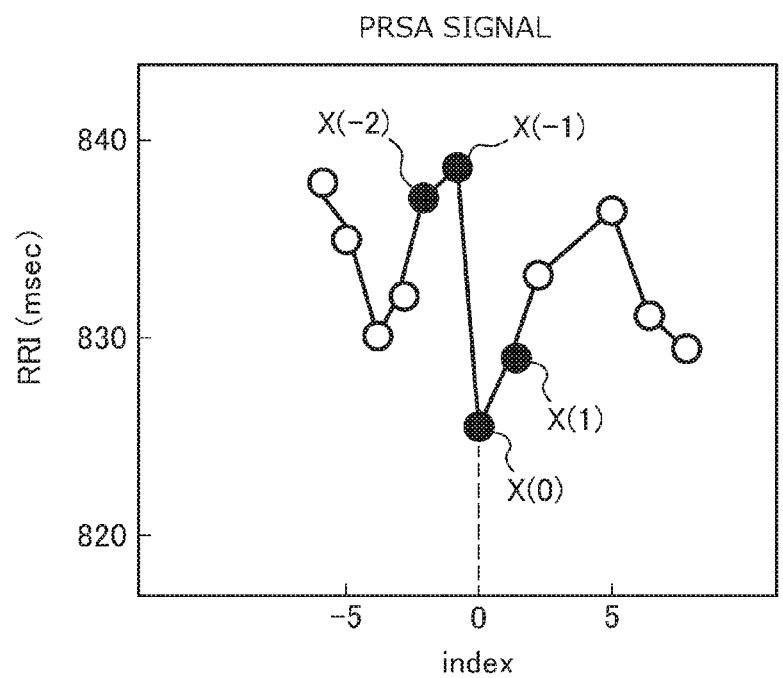
FIG. 6 is a graph of example PRSA signals obtained in such a manner that the waveforms of the FIG. 5 are averaged for each index, according to an embodiment.
Figure 7A:
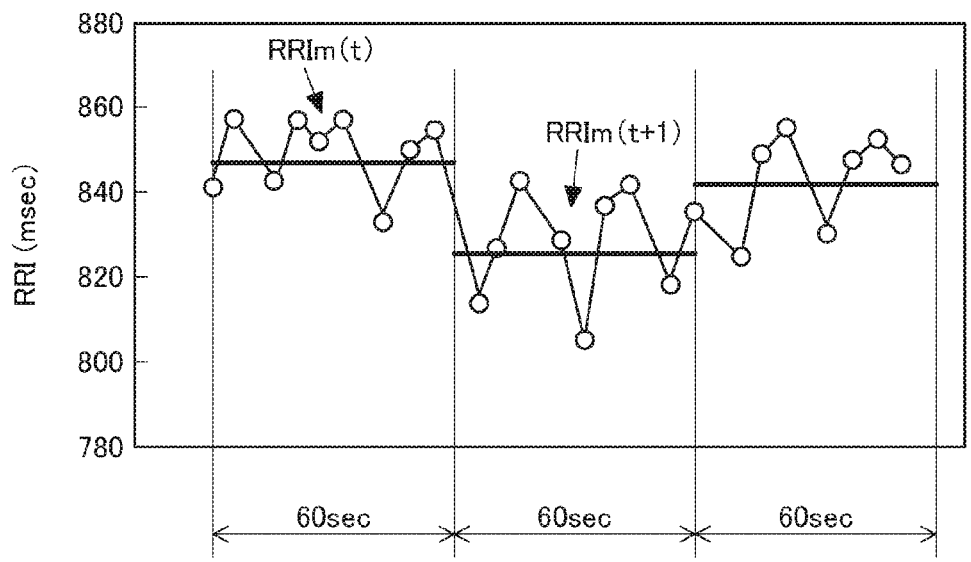
FIG. 7A is a graph of an example RRI and an example RRIm as an average of RRIs for every 60 seconds, according to an embodiment.
Figure 7B:
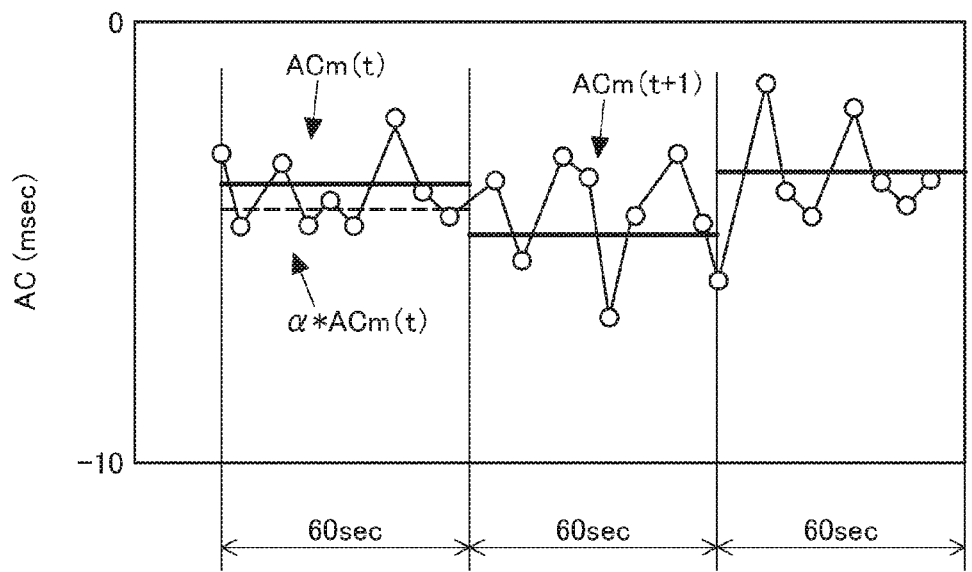
FIG. 7B is a graph of an example acceleration capacity AC, an ACm as an average of ACs for every 60 seconds, and the value obtained by multiplying an ACm (t) as an average of ACs for 60 seconds by α, according to an embodiment.

Next, a calculation method in the alertness determination processing by the alertness device 10 configured as described above is described with reference to FIGS. 2 to 7. Note that the alertness maintenance processing by the alertness device 10 is described below. FIG. 2 is a flow chart of an example of the alertness determination processing, and FIG. 3 is a graph of a pattern of an electrocardiographic waveform. Further, FIG. 4 is a graph of a chronological change in an RRI. FIG. 4 shows, as an anchor, each point where in comparison between RRIs at adjacent time points, a latter one of the RRIs is shorter than a former one of the RRIs. FIG. 5 illustrates the state in which the same number of waveforms as that of the anchors of FIG. 4 are replicated and the time axes at the anchor points of the replicated waveforms are aligned to each other. FIG. 6 is a graph of PRSA signals obtained in such a manner that the waveforms of the FIG. 5 are averaged for each index. Further, FIG. 7A is a graph of an RRI and an RRIm as an average of RRIs for every 60 seconds, and FIG. 7B is a graph of an AC, an ACm as an average of ACs for every 60 seconds, and the value obtained by multiplying an ACm (t) as the average of ACs for 60 seconds by α.

The alertness determination processing of the present embodiment is the processing executed using, as an indicator for alertness determination, an acceleration capacity (AC) (described below), which tends to be lower in association with sympathetic nerve activation occurring at an initial stage in an alertness decrease to intentionally shake off drowsiness.

The details of each processing step is described with reference to the flow of the alertness determination processing of the present embodiment. First, each heart rate sensor 20 responds to start of an engine of a vehicle or pressing of a not-shown start switch to detect a potential signal corresponding to the body potential of the seated passenger.

The potential signals detected by the heart rate sensors 20 are, as potential difference data, stored in the storage unit 72 of the control device 70 via the signal processing circuit 30. That is, the control device 70 obtains the potential difference data on the heart rate of the seated passenger (step S11).

Next, based on the potential difference data obtained by the heart rate sensors 20, the waveform generation unit 73a generates electrocardiographic waveform data taking a potential difference and a time as axes as illustrated in FIG. 3 (step S12).

Next, the calculation unit 73b calculates, from the generated electrocardiographic waveform data, an RRI as a time interval between adjacent R-waves each instantaneously showing a waveform with a great potential difference. As illustrated in FIG. 7A, the calculation unit 73b calculates an average RRIm of RRIs for every 60-second interval.

Next, the determination unit 73c compares between an RRIm (t) calculated for a certain interval and an RRIm (t+1) calculated for the subsequent interval, and then, determines whether or not the RRIm (t+1) is less than the adjacent preceding RRIm (t) (step S13).

When it is determined that the RRIm (t+1) is less than the RRIm (t) ("Yes" at step S13), the calculation unit 73b calculates phase-rectified signal averaging (PRSA) signals (step S14). When the RRIm (t+1) is equal to or greater than the RRIm (t) ("No" at step S13), the determination unit 73c determines that the seated passenger is in an alert state (step S18).

The PRSA signal is the signal obtained in such a manner that partial time-series averaging is performed for selected RRIs for a predetermined time period based on predetermined RRI change points. The method for calculating the PRSA signals is described with reference to FIGS. 4 to 6. FIGS. 4 to 6 are graphs where an RRI is taken as the vertical axis and an index indicating a chronological order is taken as the horizontal axis. As illustrated in FIG. 4, in a graph including 10 points of RRIs (i.e., a graph of RRIs based on the data on 11 heart beats), each point where a certain RRI is shorter than the adjacent preceding RRI is taken as an anchor γ1, γ2, γ3. Note that in order to reduce the influence of false data detection, an RRI(s) decreased from the adjacent preceding RRI by the value exceeding 5% is excluded from the candidates for anchor.

Next, as illustrated in FIG. 5, the same number of graphs each connecting the RRIs as that of the anchors γ1, γ2, γ3, i.e., three graphs in the present embodiment, are replicated. Then, the graphs each connecting the RRIs are moved parallel to the horizontal axis direction, and are aligned to each other such that the indices for the anchors γ1, γ2, γ3 in the horizontal axis are in phase with each other. Then, an RRI average is calculated for each index in the horizontal axis, and the RRI averages for the indices are connected together to obtain the PRSA signals illustrated in FIG. 5 and enlarged in FIG. 6. With the PRSA signals obtained by setting of the anchors γ1, γ2, γ3 and averaging for each index, the change pattern exhibiting the common characteristics between before and after an instantaneous heart rate decrease.

In the description made below, the anchors γ1, γ2, γ3 aligned to be in phase with each other are simply referred to as "anchors γ." Note that for the sake of clarity, it has been described above that the PRSA signals are calculated from three graphs each connecting the RRIs. However, the PRSA signals illustrated in FIG. 5 are an example of the signals obtained in such a manner that more graphs each connecting RRIs are replicated and synthesized together.

Next, the calculation unit 73b calculates an AC based on the calculated PRSA signals (step S15). The AC is for quantification of sympathetic nerve activity by analysis of a decrease in an averaged RRI based on PRSA signals. The AC is the value defined by the following formula 2, where a PRSA signal at a certain anchor γ is defined as "X(0)," a PRSA signal at the adjacent succeeding anchor γ of the certain anchor γ is defined as "X(1)," a PRSA signal at the adjacent preceding anchor γ of the certain anchor γ is defined as "X(−1)," and a PRSA signal at the point right before the X(−1) is defined as "X(−2)."

$$AC = \frac{X(0) + X(1) - X(-1) - X(-2)}{4} \quad \text{[Formula 2]}$$

The above-described four points of the PRSA signals are used for AC calculation, and the calculated AC is sufficient to show the decreasing trend between adjacent RRIs. However, the present disclosure is not limited to four points, and more points may be used to calculate the AC.

Next, an AC average is calculated for every 60-second interval, and is compared between adjacent intervals. Specifically, when AC averages for adjacent intervals are represented by ACm (t) and ACm (t+1) as illustrated in FIG. 7B, the α-fold of the former ACm (t) is compared with the latter ACm (t+1) (step S16). The factor α is 1.0 to 2.0, and more preferably 1.4.

When the comparison shows that the ACm (t+1) is less than the α-fold of the ACm (t) ("Yes" at step S16), it is determined that the seated passenger is in an unalert state (step S17). On the other hand, when the ACm (t+1) is equal to or greater than the α-fold of the ACm (t) ("No" at step S16), it is determined that the seated passenger is in the alert state (step S18).

Finally, the control device 70 determines whether or not there is a processing termination instruction made by, e.g., pressing of a not-shown stop switch by the seated passenger (step S19). When there is no instruction ("No" at step S19), the process returns to the step S11 of obtaining the potential difference data. When there is the processing termination instruction ("Yes" at step S19), the process is terminated.

In the alertness determination processing, the seated passenger is, as a comprehensive evaluation, not determined as being in the unalert state when both of the following conditions are not particularly satisfied: the condition where the RRIm (t+1) is less than the RRIm (t) at step S13; and the condition where the ACm (t+1) is less than the α-fold of the ACm (t) at step S16. Note that the interval for which the RRIm as the RRI average is calculated at step S13 and the interval for which the ACm as the AC average is calculated at step S16 are each 60 seconds. However, the present disclosure is not limited to the 60-second interval. Each of these intervals may be a 20- to 300-second interval. A longer interval results in a longer delay in alertness determination. However, the number of data pieces extracted for averaging each parameter increases, and therefore, the reliability of alertness determination increases.

Specific Example of Alertness Determination

Figure 9:
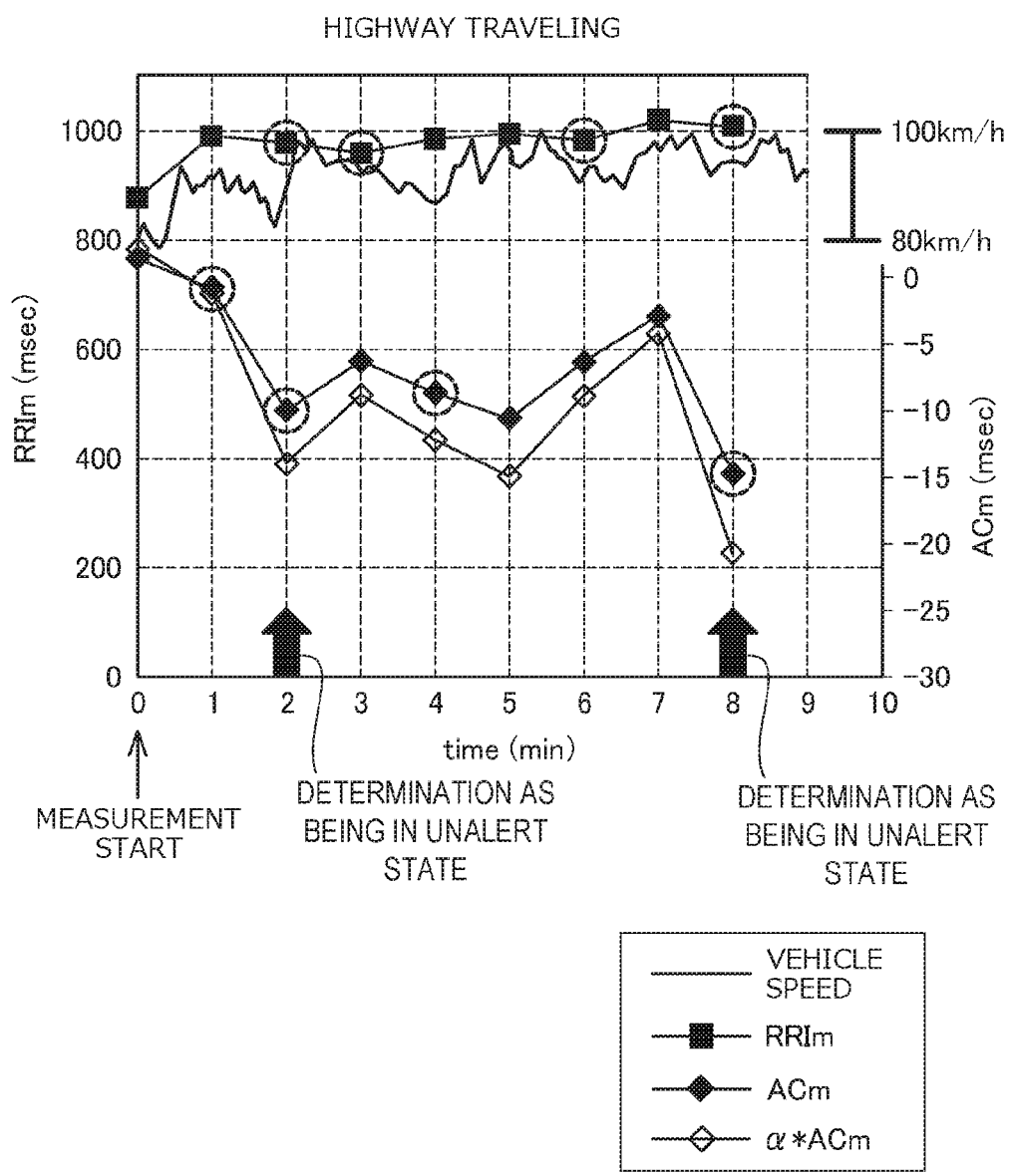
FIG. 9 is a graph of an example change in subject's RRIm and ACm in highway traveling, according to an embodiment.

Next, the flow of the above-described alertness determination processing while the vehicle including the alertness device 10 is being operated is described with reference to measurement data shown in FIGS. 8 and 9. FIG. 8 is a graph of a change in subject's RRIm and ACm in continuous curve traveling, and FIG. 9 is a graph of a change in subject's RRIm and ACm in highway traveling.

In these figures, the RRIm shown at each point of the graph is an RRI average obtained for one minute after such a point. Similarly, the ACm shown at each point of the graph is an AC average obtained for one minute after such a point. Particularly in alertness determination of the present measurement process, a constant α for comparison between ACms of adjacent intervals is set at 1.4, and is shown at each graph for alertness evaluation.

Data in Continuous Curve Traveling

First, the RRIm in continuous curve traveling is described. In FIG. 8, the RRIms at the points of two minutes and seven minutes are each surrounded by a dashed circle.

As shown in FIG. 8, the RRIm at the point of two minutes, i.e., the point showing the interval right after the interval for the point of one minute, is less than the RRIm at the point of one minute. Moreover, the RRIm at the point of seven minute, i.e., the point showing the interval right after the interval for the point of six minutes, is less than the RRIm at the point of six minutes. That is, the RRIm condition determined as the unalert state is satisfied at the points surrounded by the dashed circles.

Further, the ACm in continuous curve traveling is described. The ACm at the point of eight minutes is surrounded by a dashed circle. As shown in FIG. 8, the ACm at the point of eight minutes, i.e., the point showing the interval right after the interval for the point of seven minutes, is less than the α-fold of the ACm at the point of seven minutes. That is, the ACm condition determined as the unalert state is satisfied at the point surrounded by the dashed circle.

However, if both of the RRIm and ACm conditions determined as the unalert state are not satisfied at the same interval as described above, the seated passenger is not determined as being in the unalert state as the comprehensive evaluation. As a result, the data of FIG. 8 shows that in continuous curve traveling, the subject is not determined as being in the unalert state across the entire intervals. In other words, it is determined that the alert state is maintained.

Data in Highway Traveling

Next, the RRIm in highway traveling is described. In FIG. 9, the RRIms at the points of two minutes, three minutes, six minutes, and eight minutes from the beginning of measurement are each surrounded by a dashed circle. As shown in FIG. 9, each of the RRIms at the points of two minutes, three minutes, six minutes, and eight minutes, i.e., each point showing the interval right after the interval for the adjacent preceding point, is less than the RRIm at the adjacent preceding point. The RRIm condition determined as the unalert state is satisfied at these points surrounded by the dashed circles.

Further, the ACm in highway traveling is described. The ACms at the points of one minute, two minutes, four minutes, and eight minutes from the beginning of measurement are each surrounded by a dashed circle. Each of the ACms at the points of one minute, two minutes, four minutes, and eight minutes, i.e., each point showing the interval right after the interval for the adjacent preceding point, is less than the α-fold of the ACm at the adjacent preceding point. The ACm condition determined as the unalert state is satisfied at these points surrounded by the dashed circles.

Both of the RRIm and ACm conditions determined as the unalert state are satisfied at the points of two minutes and eight minutes. Thus, in highway traveling, the subject is, as the comprehensive evaluation, determined as being in the unalert state at the points of two minutes and eight minutes.

Alertness Maintenance Processing

Next, the alertness maintenance processing for driving the vibration motor M according to the determination result as the unalert state in the above-described alertness determination processing is described. First, each heart rate sensor 20 responds to start of the engine of the vehicle or pressing of the not-shown start switch to detect a potential signal corresponding to the body potential of the seated passenger.

The potential signals detected by the heart rate sensors 20 are, as potential difference data, stored in the storage unit 72 of the control device 70 via the signal processing circuit 30. That is, the control device 70 obtains the potential difference data on the heart rate of the seated passenger (step S21).

Next, based on the potential difference data obtained by the heart rate sensors 20, the waveform generation unit 73a generates electrocardiographic waveform data taking a potential difference and a time as axes as illustrated in FIG. 3 (step S22).

Next, the calculation unit 73b calculates, from the generated electrocardiographic waveform data, an RRI as a time interval between adjacent R-waves each instantaneously showing a waveform with a great potential difference. As illustrated in FIG. 7A, the calculation unit 73b calculates an average RRIm of RRIs for every 60-second interval.

Next, the determination unit 73c compares between a certain calculated RRIm (t) and an RRIm (t+1) calculated as an average for the next 60-second interval, and then, determines whether or not the RRIm (t+1) is less than the adjacent preceding RRIm (t) (step S23).

When the determination unit 73c determines that the RRIm (t+1) is equal to or greater than the RRIm (t) ("No" at step S23), the process returns to step S21 of obtaining the potential difference data. When the determination unit 73c determines that the RRIm (t+1) is less than the RRIm (t) ("Yes" at step S23), the calculation unit 73b calculates PRSA signals (step S24).

Further, the calculation unit 73b calculates an AC based on the calculated PRSA signals (step S25).

Next, an AC average is calculated for every 60-second interval, and is compared between adjacent intervals. Specifically, when AC averages for adjacent intervals are represented by ACm (t) and ACm (t+1) as illustrated in FIG. 7B, the α-fold of the former ACm (t) is compared with the latter ACm (t+1) (step S26). The factor α is 1.0 to 2.0, and more preferably 1.4.

When the comparison shows that the ACm (t+1) is equal to or greater than the α-fold of the ACm (t) ("No" at step S26), the process returns to the step S21 of obtaining the potential difference data. On the other hand, when the ACm (t+1) is less than the α-fold of the ACm (t) ("Yes" at step S26), the driver 73d drives the vibration motor M (step S27).

The driver 73d continuously drives the vibration motor M for a predetermined period of time (step S28), and then, stops the vibration motor M (step S29).

Finally, the control device 70 determines whether or not there is a processing termination instruction made by, e.g., pressing of the not-shown stop switch by the seated passenger (step S30). When there is no instruction ("No" at step S30), the process returns to the step S21 of obtaining the potential difference data. When there is the processing termination instruction ("Yes" at step S30), the process is terminated.

When the RRIm and ACm conditions indicating lowering of the alertness of the seated passenger are satisfied, the vibration motor M can be driven to provide stimulation to the seated passenger in the alertness maintenance processing. Thus, the alertness of the seated passenger can be effectively maintained.

Note that the interval for which the RRIm as the RRI average is calculated at step S23 and the interval for which the ACm as the AC average is calculated at step S26 are each 60 seconds. However, the present disclosure is not limited to the 60-second interval. Each of these intervals may be a 20- to 300-second interval. A longer interval results in a longer delay in alertness determination. However, the number of data pieces extracted for averaging each parameter increases, and therefore, the reliability of alertness determination increases.

In the above-described embodiment, the ACm as the comparison target in alertness determination is compared between adjacent intervals in alertness determination, the ACm being the average obtained by division by a constant of four, i.e., the number of indices X(1), X(−1), X(0), X(−2) of the PRSA signals. In the case where the AC is compared between adjacent intervals, the common constant, i.e., a constant of four, is presented between adjacent intervals. For this reason, a constant of four as the denominator of the formula for defining the AC is not necessarily required. Thus, the AC average is not compared between adjacent intervals, but an average of ACn defined by the following formula 2 may be compared.

$$ACn = X(0) + X(1) − X(−1) − X(−2) \quad \text{[Formula 1]}$$

In the present embodiment, the alertness device, the seat, and the alertness determination method according to the present disclosure have been mainly described. Note that the above-described embodiment has been merely set forth as an example for the sake of easy understanding of the present disclosure, and does not limit the present disclosure. Change and modification can be made to the present disclosure without departing from the gist of the present disclosure, thus the present disclosure include all equivalents.

For example, in the above-described embodiment, it has been described that when the alertness device determines the seated passenger as being in the unalert state, the vibration motor M provides stimulation to the seated passenger. However, the present disclosure is not limited to the notification method using stimulation, and the unalert state may be notified by other methods. For example, when the alertness device determines the seated passenger as being in the unalert state, alarm sound may be emitted from a speaker, or light may be emitted from a light emitter. Further, an image may be displayed on a display placed inside the vehicle.

In the above-described embodiment, the vehicle seat which can be mounted on the automobile has been described as a specific example. However, the present disclosure is not limited to such a vehicle seat. The present disclosure can be used as a seat for a vehicle such as an airplane or a ship. In addition, the present disclosure may be employed for seats at movie theaters and stage theaters and seats for relaxation, for example.

REFERENCE SIGNS LIST

S: vehicle seat
  1: seat cushion
  2: seat back
10: alertness device
  20: heart rate sensor
  30: signal processing circuit
  70: control device
    72: storage unit
    73a: waveform generation unit
    73b: calculation unit
    73c: determination unit
    73d: driver
M: vibration motor

The invention claimed is:

1. An alertness device comprising:
a heart rate sensor configured to obtain an electrocardiographic signal of a person;
a calculation unit configured to calculate the electrocardiographic signal obtained from the heart rate sensor;
a waveform generation unit configured to generate, from an electrocardiographic waveform of the electrocardiographic signal, an RRI waveform showing transitions for a predetermined time period with RRIs, each RRI of the predetermined time period being an R-R interval between R-waves of the electrocardiographic waveform; and
a determination unit configured to determine an alertness state of the person based on the electrocardiographic signal;
wherein the calculation unit replicates a same number of RRI waveforms as that of anchors, each anchor being a point where a certain RRI is shorter than an adjacent preceding RRI in the RRI waveform generated by the waveform generation unit, moves time axes of the replicated RRI waveforms such that the anchors of the replicated RRI waveforms are in phase with each other, and calculates a phase-rectified signal averaging (PRSA) signal, which is an RRI average for each time axis of the replicated RRI waveforms; and
wherein the determination unit determines, based on the RRIs and the PRSA signals, whether the person is in an alert state or an unalert state.

2. The alertness device of claim 1,
wherein the waveform generation unit generates a PRSA signal waveform based on the PRSA signals, and
wherein when an ACn is defined by $$ACn = X(0) + X(1) − X(−1) − X(−2),$$

where in the generated PRSA signal waveform, a PRSA signal at a certain anchor is defined by X(0), a PRSA signal for a heart rate at an adjacent succeeding anchor of the certain anchor is defined by X(1), a PRSA signal for the heart rate at an adjacent preceding anchor of the certain anchor is defined by X(−1), and a PRSA signal for the heart rate at an adjacent preceding anchor of the anchor at which the X(−1) is obtained is defined by X(−2),
the calculation unit calculates, for a predetermined time period, the RRI average and an ACn average, and
the determination unit determines, based on the values calculated by the calculation unit, that the person is in the unalert state when a certain RRI average is less than an adjacent preceding RRI average and when a certain ACn average is less than an α-fold of an adjacent preceding ACn average.

3. The alertness device of claim 2, wherein an α is 1.0 to 2.0.

4. The alertness device of claim 2,
wherein the calculation unit calculates the RRI average and the ACn average for every 20- to 300-second interval, and
wherein the determination unit determines the alertness state of the person based on the RRI average and the ACn average calculated by the calculation unit.

5. The alertness device of claim 2, wherein an α is 1.4.

6. The alertness device of claim 4, wherein the calculation unit calculates the RRI average and the ACn average for every 60-second interval.

7. The alertness device of claim 1, further comprising:
a notification device configured for notification to the person or one or more persons therearound; and
a driver configured to drive the notification device to notify the person or the one or more persons therearound of the determination unit having determined that the person is in the unalert state.

8. A seat comprising:
a seat cushion configured to be seated on by a passenger;
a seat back configured to be a back rest of the passenger when the passenger is seated on the seat cushion; and
the alertness device of claim 1,
wherein the heart rate sensor is disposed in the seat back.

9. A method for determining alertness, comprising:
obtaining an electrocardiographic signal;
generating, from an electrocardiographic waveform of the electrocardiographic signal, an RRI waveform showing transition for a predetermined time period with RRIs, each RRI being an R-R interval between R-waves;
replicating the same number of RRI waveforms as that of anchors, each anchor being a point where a certain RRI is shorter than an adjacent preceding RRI in the generated RRI waveform;
moving time axes of the replicated RRI waveforms such that the anchors of the replicated RRI waveforms are in phase with each other;
calculating a PRSA signal defined as an RRI average for each time axis; and
determining, based on the RRIs and the PRSA signals, whether a person is in an alert state or an unalert state.

10. The method of claim 9,
wherein a PRSA signal waveform is generated based on the PRSA signals, and
wherein in a case where an ACn is defined by $$ACn = X(0) + X(1) - X(-1) - X(-2),$$

where in the generated PRSA signal waveform, a PRSA signal at a certain anchor is defined by $X(0)$, a PRSA signal at an adjacent succeeding anchor of the certain anchor is defined by $X(1)$, a PRSA signal at an adjacent preceding anchor of the certain anchor is defined by $X(-1)$, and a PRSA signal at an adjacent preceding anchor of the anchor at which the $X(-1)$ is obtained is defined by $X(-2)$,
the RRI average and an ACn average are calculated for a predetermined time period, and
based on the calculated values, the person is determined as being in the unalert state when a certain RRI average is less than an adjacent preceding RRI average and when a certain ACn average is less than an $\alpha$-fold of an adjacent preceding ACn average.

* * * * *